United States Patent [19]

Hall-Hibbitts et al.

[11] Patent Number: 5,902,589
[45] Date of Patent: May 11, 1999

[54] METHOD FOR TREATING HYDRATABLE POLYMERS, COMPOSITIONS OBTAINED THEREFROM, AND METHODS OF USING SAME

[75] Inventors: John E. Hall-Hibbitts; Maria E. Gonzalez-Miller, both of Austin, Tex.

[73] Assignee: Conagro, Inc., Guatemala

[21] Appl. No.: 08/982,092

[22] Filed: Dec. 1, 1997

Related U.S. Application Data

[60] Division of application No. 08/535,490, Sep. 28, 1995, Pat. No. 5,720,967, which is a continuation-in-part of application No. 08/203,477, Feb. 28, 1994, abandoned, which is a continuation of application No. 07/874,709, Apr. 28, 1992, abandoned.

[51] Int. Cl.$^6$ .................................................. A01N 25/10
[52] U.S. Cl. .................. 424/400; 424/78.06; 424/78.09; 424/78.18; 424/78.31; 424/78.32; 424/78.33; 424/78.34; 424/78.35; 424/78.36; 424/78.37; 424/78.38; 424/401; 424/405; 424/406; 424/407; 424/408; 424/409; 424/410; 424/411; 424/443; 424/484; 424/489; 514/772.3; 514/777; 514/784; 514/785

[58] Field of Search ...................................... 424/405, 406, 424/407, 408, 409, 410, 411–413, 443, 484–488, 489, DIG. 13, 78.06, 78.09, 78.18, 78.31–78.38, 400, 401; 514/772.3–772.7, 777–781, 784, 785

[56] References Cited

U.S. PATENT DOCUMENTS

| | | | |
|---|---|---|---|
| 4,906,488 | 3/1990 | Pera | 426/573 |
| 4,985,251 | 1/1991 | Levy | 424/404 |

*Primary Examiner*—Neil S. Levy
*Attorney, Agent, or Firm*—James F. Weiler

[57] ABSTRACT

Aqueous solutions of hydratable polymers are prepared by hydrating a hydratable polymer in water without agitation sufficient to shear the molecular structure of the polymer thereby maintaining intact the polymer's molecular structure thereby providing a structurally uniform composition. The resulting solutions are sticky and tacky and are useful in controlling insects and for other uses. The resulting solutions can be dried to form powders. The resulting products readily degrade, are non-toxic, and non-ionic, and hence environmentally benign.

16 Claims, No Drawings

METHOD FOR TREATING HYDRATABLE POLYMERS, COMPOSITIONS OBTAINED THEREFROM, AND METHODS OF USING SAME

CROSS-REFERENCE TO RELATED APPLICATION

The present application is a division of application Ser. No. 08/535,490 filed Sep. 28, 1995, now U.S. Pat. No. 5,720,967, which is a continuation-in-part of U.S. patent application, Ser. No. 08/203,477 filed Feb. 28, 1994, now abandoned, which is a continuation of U.S. patent application Ser. No. 07/874,709 filed Apr. 28, 1992, now abandoned.

FIELD OF THE INVENTION

The present invention is in the field of hydratable polymers, compositions obtained therefrom and methods of using them.

BACKGROUND OF THE INVENTION

The present invention is directed to a method of treating hydratable polymers, compositions obtained therefrom having properties and uses not possible or recognized previously, and methods of using them. In the past, aqueous compositions of hydratable polymers have been prepared by methods using significant agitation which shears the polymers' repeating molecular structure resulting in products which are irregular and not of uniform structural compositions. While the materials obtained from such processes are useful products in a number of fields, there are certain areas where such nonuniform and irregular structural compositions have not been useful.

The present invention provides a method of treating hydratable polymers and the resulting compositions in which their structural repeating molecules are intact rather than sheared which results in hydrated polymer compositions having properties not recognized previously and effective for uses for which sheared structural polymer compositions are not useful.

SUMMARY OF THE INVENTION

In accordance with the present invention, an aqueous composition of hydratable polymer is prepared by placing polymer powder into water and then hydrating the composition for a period of time without agitation sufficient to shear the structural arrangement of the polymer molecules. This results in an aqueous composition which the polymer structure is uniform and the repeating structural molecules are intact and not sheared. The resulting composition is rather sticky and viscous and serves as a base material for making sheets' end products having various physical properties, microencapsulating various chemical substances, and making dry powders and sprays. Advantageously, the resulting compositions can be used to form a floating film which is an effective insecticide against water-borne, syphontube breathing insects. The resulting composition shows excellent wetting characteristics and thus also can be used as an insecticide applicable to vegetation, as a vehicle for chemical agents, to microencapsulate chemicals and for other uses.

The resulting composition can be dried to form powders and solid films. The powders themselves are useful insecticides against various kinds of crawling insects or again can be used as vehicles for chemical agents. The powders and solid films can be used as hemostatic materials, which optionally may be provided with additional therapeutic agents, as burn-treating agents, and as a surface-protecting layer for painted or finished surfaces. The solid films may also be layered to provide three-dimensional objects, such as carriers for beverage containers. Because of the ready hydration of the materials, used or excess film or powder can be readily recycled. Also due to the ready hydration, the material readily breaks down in nature, and thus minimizes environmental damage.

DETAILED DESCRIPTION OF THE INVENTION

In accordance with the present invention, the aqueous composition of hydrated polymer is prepared by placing the powdered hydratable polymer in water and then allowing the polymer to hydrate for a period of time (age), without agitation sufficient to shear the molecular structure for a period of time sufficient for the polymer to be hydrated in the water. The hydration is preferably carried out at ambient temperatures, e.g. about 25° C. although raised temperatures are also possible. The hydration preferably is conducted in a sealed container to prevent contamination, since bacteria have been found to degrade the material. Ultraviolet (UV) stabilizers can be included or exposure to sunlight minimized since UV radiation tends to degrade the composition. As previously mentioned, the structural molecular arrangement of the hydrated polymers in the resulting composition is intact, not sheared, and thus has a uniform structural composition. The resulting hydrated polymer material is thick, sticky, and viscous and serves as a base for making various products having desired properties as hereinafter described.

Synthetic or naturally occurring hydratable polymers can be used in the invention. It is not required that the polymer hydrate quickly in water, only that it be capable of hydration. Examples of suitable polymers include polyethylene oxide polymers, alkyl- and hydroxyalkyl cellulose polymers, sodium carboxymethyl cellulose, hydroxyethyl- and hydroxypropyl cellulose, polyacrylamide, polyacrylic acid) polyvinyl alcohol, polyvinyl pyrollidone, xanthin gum, starch, corn starch, dry starch, and natural gums such as locust bean gum, guar gum, and others. Poly(ethylene oxide), high molecular weight hydroxypropyl cellulose and high molecular weight polyacrylamides are particularly useful and are preferred.

The polymers utilized can have a wide range of molecular weights. For example, hydratable polymers having molecular weights from 100,000 to 6,000,000 and coagulant grades may be used. As discussed below, the molecular weights are selected depending upon the desired properties of the final composition and blends of materials used. Increasing the component of high molecular weight polymers will provide a more viscous composition which forms a stronger film upon drying. Lower molecular weight polymers provide a less viscous solution, which forms a more flexible film. The amount of the polymer added to water is about 10 to 40 percent by weight, preferably about 20 percent by weight.

The aging time will vary depending upon the molecular weight of the material. For molecular weights in the lower ranges, for example around 100,000, the aging time is about five days. When the molecular weight is increased to the neighborhood of 1,000,000, the aging time is increased to seven days. For molecular weights of 2,000,000 to 4,000,000 ten days' aging may be necessary. For the very high molecular weight materials, for example having molecular weights of about 5,000,000 or more, twelve days may be necessary. The aging time is selected so as to allow the polymer to be completely hydrated substantially without agitation, although some minor amounts of agitation may be permitted. The aging without agitation and hence not shearing the polymer's molecular structure is believed to permit certain interactions between the hydrated polymer molecules which are inhibited by the shearing forces commonly employed to hydrate such polymers.

After the aging is completed, a small amount of a lower alcohol, for example isopropanol in the amount of 2 percent by weight of the polymer, can be added to the composition. This can be followed by mild agitation if necessary to complete mixing, for example, at the rate of 60–200 rpm, with the higher mixing rate being applied to the lower molecular weight materials and vice versa. The lower alcohol acts as a bactericide and also assists in subsequent blending operations. After the addition of the lower alcohol, the resulting composition can be aged for 24 hours and then blended with material of other molecular weights or other additives to form desired final compositions.

The aqueous compositions thus obtained are molecularly and structurally uniform, and are relatively viscous and sticky. The compositions will float on water and spread readily. Therefore, the solutions function as effective insecticidal films against water-borne syphon-tube breathing insects such as mosquito larvae. For this use, the initial compositions are diluted to provide a final polymer level of about 0.1 to 5 percent by weight, preferably about 0.3 to 1 percent by weight. When applied to an insect breading area, such as shallow lake shore or swamp areas, the thus-diluted composition quickly spreads to form a thin, sticky film on the surface of the water, which prevents the water-borne insects from breathing properly. This is effective in quickly killing the insects.

However, the film thus formed will disperse readily and degrade and is not harmful to other life forms in the area. The life of the film will be longer with higher amounts of polymer. The length of the life of the film can also be extended by addition of an ultraviolet inhibitor such as lignine. Thus, the material can be used to form a liquid boom, useful in containing oil spills.

The aqueous polymer composition also exhibits excellent wetability and readily spreads across surfaces. Therefore, the material forms a sticky layer when applied to vegetation, thus trapping and immobilizing pests upon the vegetation. The excellent wetability exhibited by the composition permits leaf surface coverages of up to 70 or 80 percent as compared to the 1 to 2 percent coverage found with powder and mist application of pesticides even with waxy-surfaced leaves. The terrestrial insecticide solution may be prepared by diluting the original polymer composition on the order of about five times, and therefore the terrestrial insecticide will have a higher polymer concentration than the insecticide against the water-borne insects. The stickiness of the solution immobilizes pests on the vegetation preventing them from eating and making them easy prey for birds and other predators. Again, the material readily degrades and thus does not present long-term environmental concerns. The wetting characteristics also make the material useful as a vehicle for delivering other insecticidal agents permitting the more efficient application of such agents and reducing the overall amount of pesticide released into the environment.

The aqueous composition can be dried to form a solid material having properties not present in the polymer from which it was obtained. For example, the aqueous composition can be dried to form a powder which has insecticidal properties. The powder has been found to adhere to the diaphanous membrane joints connecting the chitin sections of insect bodies, as well as to the insect antennae and wings. The material acts as an irritant, interrupting the normal activities of the insect, and also interferes with the insect's sensory organs and eating and digestive functions. The powder becomes tacky when moist, and thus the insect's activities in attempting to rid itself of the powder can actually result in the accumulation of even more powder, until the insect becomes encased in the powder. The powder form is particularly effective against crawling insects and nesting insects, since the powder can be easily applied to such insects. The powder can also be used as a carrier for chemical insecticides.

Since the powder readily rehydrates, the powder form can also be applied in appropriate amounts to create the floating insecticidal film against water-borne insects discussed above. The powder form provides readily apparent advantages in terms of shipping and handling costs. Whether applied as powder or liquid, the material should be applied to the surface of the water in a finely divided form so as not to break the surface of the water. This permits the formation of the film on the surface.

The aqueous composition also can be dried to form solid films. Films are prepared by simply spreading the aqueous composition and subjecting it to mild heating if desired. It is not necessary to drive off all of the water from the aqueous composition when forming the powder or solid film. Some residual water, e.g. an amount equivalent to the atmospheric moisture, can be tolerated. The films are non-toxic, non-ionic, and readily degrade with water. The solid films are breathable and exhibit hemostatic properties as well as utility in protecting skin for burn treatment. The hemostatic properties can also be employed by impregnating a carrier material, e.g. gauze fabric, with a powder of the dried polymer, so that the powder will contact the wound when the wound is covered with the gauze.

The solid films can be used also as packaging materials, for example as trash bags or for toxic materials which will be added to water for use. The rehydration of the solid film permits the release of the material contained at the desired time.

The solid film can be used as a cover for disposable diapers and similar products such as panty shields, sanitary napkins and tampon applicators. The solid film can be used as seed tapes for agriculture and also exhibit some soil regenerative properties. The solid film can also provide protective coatings for finished surfaces, such as furniture or automobiles. The coating material is highly resistant to impact and scratching. Higher molecular weight materials are particularly useful for this latter application. As a further application, freshly-picked fruit can be dipped in the aqueous composition and dried. The thin film which remains on the fruit after drying retards respiration and the ripening process thereby extending the shelf and shipping life of the fruit. The film also protects fruit and other produce from bruising. Since the solid film readily hydrates, it is easily washed from the produce.

The films also can be laminated to form three-dimensional objects which are readily degradable. This can be easily applied, for example, to items such as beverage can holders. Because the material can be readily hydrated, any used products or excess solid material can simply be rehydrated for recycling if desired. It has been found that recycled material even tends to have improved properties, for example in terms of ductility, elasticity and impact resistance, as compared to the original material.

In the following examples compositions of hydrated polyethylene oxide having molecular weights of 100,000, 1,000,000, 2,000,000, 4,000,000 and 6,000,000 are prepared in accordance with the process discussed above and used to make the following products.

EXAMPLE 1

In this example, a base polymer, polyethylene oxide, having a molecular weight of over 100,000 in an amount of 5 percent by weight was allowed to hydrate in water for a period of 180 hours without agitation sufficient to shear the molecular polymer structure. After slowly hydrating or curing, the resulting material was thick, sticky, and was difficult to handle. This base material serves as a base for preparing various end products set forth herein as well as other uses. Good results are obtained by hydrating 2.5 to 50 percent boy weight.

EXAMPLE 2

The sticky viscous material was poured to a thin film and dried for 1 hour at 25 to 45° C., such as uniformly pouring over a glass surface and then allowing it to dry in a dry environment for approximately 4 hours. The resulting solid film was easily peeled off the glass surface, and the finished product sheet was ready for conversion to an end product, such as a C strip for forming degradable containers or bags, degradable plastic like pouches or small envelopes to be filled with chemical substances. By varying the thickness of the original pour, solid films of different desired thicknesses were obtained. Good results are obtained by diluting the base material up to 20 percent by weight and then allowing it to dry on a surface.

EXAMPLE 3

In this example, the base material of example 1 is utilized to microencapsulate or entrain chemical substances. The base material was diluted 30 percent by adding ordinary tap water to it. An antibiotic such as penicillin or carbolic based antiseptic, methylate, was added to and mixed with the diluted base material. The resulting product can be used in either liquid or dry form which results in an excellent insecticide. Good results are obtained by diluting the base material by 20 to 40 percent by weight.

EXAMPLE 4

Powders were prepared from the hydrated compositions discussed previously. A solid insecticidal composition against water-borne insects was prepared by mixing about 30 percent by weight of a pulverized 100,000 molecular weight polymer and 70 percent be weight of a pulverized 4,000,000 molecular weight polymer. Volcanic ejecta and/or talc was used as environmentally benign carriers or extenders for the resulting mixture of powders. When applied to the surface of water, in amounts to provide a final concentration in the range of about 100–600 ppm, the polymer powders rapidly rehydrate to form a floating film on the surface, which acts as an insecticide against syphon-tube breathing insects in the water.

EXAMPLE 5

Aqueous compositions of 100,000 (30 percent), 1,000,000 (30 percent) and 4,000,000 (40 percent) molecular weight materials were mixed as in Example 1. Fresh-picked fruit was dipped in the resulting composition and then dried, resulting in a thin film of about 80 microns being formed on the fruit. The film retarded the respiration cycle of the fruit, thereby controlling the ripening process and extending the shipping and shelf life of the fruit up to 100 percent. Mangoes, bananas, and pears were particularly responsive to such treatment.

EXAMPLE 6

A topical hemostat was prepared by mixing 80 percent by weight of hydrated polymer of molecular weight 1,000,000 and 20 percent by weight of corn starch powder. The corn starch accelerated the gelling of the hydrated polymer, which in turn protects the wound and accelerates coagulation.

EXAMPLE 7

The thin solid film made in accordance with example 2 had its physical characteristics enhanced by increasing ductility, elasticity, and impact resistance. In other words a tougher film was produced by adding 25 percent by weight of collagen material, such as Knoxes Table gelatin. The resulting film was still degradable.

EXAMPLE 8

In this example, the base material of example 1 was combined with each of xanathan gum, starch, corn starch, dry starch, locust bean gums or combinations thereof, at the rate of 15 to 20 percent by weight. Each of the gums and starches or combinations of them produced a thin, solid film whose characteristics were different. The resulting films had more elasticity, greater impact resistance and can be tailored to the end use product specifications.

EXAMPLE 9

In this example, the water soluble polymer composition in powder or liquid form was utilized to control fire ant populations. Preferably, the composition of example 4 was applied directly to the ant hill by a dusting machine to this entrance hole, the exterior of the mound, and the area surrounding the mound for a diameter of approximately six feet. After the initial application three days layer, a second application of the composition of example 4 was applied, and no fire ants were encountered. Similar results were obtained utilizing the aqueous composition of example 5.

By way of summary, when the resulting hydrated material is used in liquid form, it can be sprayed or spread on the surface of water to kill insects, such as mosquito larvas (siphon breathers), it helps stick chemicals to plant surfaces, leaves, and the like, it spreads over and sticks to plant surfaces to provide uniform coverage; it can have other chemical compounds added to its liquid state, such as insecticides, pesticides, and antifungal agents that prevent spread of fungi as well as other maladies found in crop cultivation; when the liquid is dry, it forms a very fine, thin, solid film on the plant surfaces, which will not damage the host, but stops the spread of fungi by preventing the organism from obtaining any moisture required for its development, while there are generally two types of plant leaf surfaces, those which are easy to wet and those which are very difficult to wet, the liquid material spreads itself and any insecticides microencapsulated in it or fungicides over the leaf surface which kill the insects, which in past the insects were not effected by only spreading insecticides or fungicides over these leaf surfaces; however, the hydrated polymer film with designed molecular weight overcomes surface tension to the extent that it spreads over the surfaces.

Accordingly, the present invention is well suited and adapted to obtain the objects and ends mentioned as well as others inherent therein.

While a detailed description of presently preferred embodiments of the invention has been set forth for purposes of disclosure, modifications thereof will be apparent to those skilled in the art which are within the spirit of the invention as defined in the following claims.

We claim:

1. An aqueous composition having a hydrated polymer dispersed therein, the hydrated polymer selected from the group consisting of polyethylene oxide, alkyl- and hydroxyalkyl cellulose polymers, sodium carboxymethyl cellulose, hydroxyethyl- and hydroxypropyl cellulose, polyacrylamide, polyacrylic acid, polyvinyl alcohol, polyvinyl pyrrolidone, xanathan gum, starch, corn starch, dry starch, locust bean gum and guar gum, the amount of the polymer being from about 2.5 to 50 percent by weight of the aqueous composition;

the hydrated polymer having been aged in water for a period of at least five days until hydrated without agitation sufficient to shear its molecular structure thereby maintaining its molecular structure intact and uniformly dispersed therein, and the aqueous polymer composition effective when applied for use in controlling water-borne insects, protecting vegetation from insects, controlling blood loss from a wound, covering a burn, providing a film protecting a surface of an object from damage, and controlling ripening of fresh fruit by providing a film around the fruit.

2. An aqueous composition having a hydrated polymer dispersed therein, the hydrated polymer selected from the group consisting of polyethylene oxide, alkyl- and hydroxyalkyl alkyl cellulose polymers, sodium carboxymethyl cellulose, hydroxyethyl- and hydroxypropyl cellulose, polyacrylamide, poly(acrylic acid), polyvinyl alcohol, polyvinyl pyrrolidone, xanathan gum, starch, corn starch, dry starch, locust bean gum and guar gum, the amount of the polymer being from about 2.5 to 50 percent by weight of the aqueous composition;

the hydrated polymer having been aged in water for a period of at lest five days until hydrated without agitation sufficient to shear its molecular structure thereby maintaining its molecular structure substantially intact, and an insecticidal chemical dispersed throughout the aqueous composition in an amount sufficient to kill insects.

3. The aqueous composition of the hydratable polymer composition of claim 1 diluted with water in a ratio of 20 to 40 percent by weight.

4. The aqueous composition of claim 1 dried to a solid polymer material.

5. The aqueous composition of claim 1 dried to form a powder.

6. The aqueous composition of claim 1 dried to form a film.

7. A method of controlling water-borne insects comprising adding to a body of water inhabited by the insects an amount of the aqueous composition of claim 3 effective to form a film on the body of water which disrupts the breathing of the water-borne insects.

8. A method of controlling insects, comprising applying to vegetation subject to attack by the insects an amount of the aqueous composition of claim 3, effective to protect the vegetation from the insects.

9. The method of claim 8, wherein the composition further includes an encapsulated insecticidal chemical.

10. A method of controlling insects, comprising applying to the insects an effective amount of the powder of claim 5.

11. The method of claim 10, wherein the hydratable polymer powder composition includes an insecticidal chemical encapsulated therein.

12. A method of controlling blood loss from a wound comprising covering the wound with the film of claim 6.

13. A method of protecting a wound comprising covering the wound with a fabric impregnated with the powder of claim 5.

14. A method of treating a burn comprising covering the burn area with the film of claim 6.

15. A method of protecting a surface from damage comprising covering the surface with the film of claim 6.

16. A method of controlling the ripening of fresh fruit comprising covering the fruit with the film of claim 6.

\* \* \* \* \*